United States Patent
Sacco et al.

(10) Patent No.: US 8,162,922 B2
(45) Date of Patent: Apr. 24, 2012

(54) CUI-TAGGED CATHETER DEVICES AND SYSTEM

(76) Inventors: John S. Sacco, Fayetteville, NY (US); Brett B. Greenky, Manlius, NY (US)

( * ) Notice: Subject to any disclaimer, the term of this patent is extended or adjusted under 35 U.S.C. 154(b) by 484 days.

(21) Appl. No.: 12/535,934

(22) Filed: Aug. 5, 2009

(65) Prior Publication Data

US 2009/0315684 A1 Dec. 24, 2009

Related U.S. Application Data

(63) Continuation-in-part of application No. 12/116,579, filed on May 7, 2008.

(51) Int. Cl.
*A61M 25/00* (2006.01)

(52) U.S. Cl. .......................................... 604/523; 705/2

(58) Field of Classification Search .................... 604/19, 604/48, 93.01, 264, 317, 319, 327, 500, 523, 604/540, 544; 235/380, 385, 492; 340/572.1, 340/572.8; 705/2–3; 600/300, 407, 437; 700/214–215; 606/1, 34

See application file for complete search history.

(56) References Cited

U.S. PATENT DOCUMENTS

| | | | | |
|---|---|---|---|---|
| 2004/0008123 | A1* | 1/2004 | Carrender et al. | 340/825.49 |
| 2006/0065713 | A1* | 3/2006 | Kingery | 235/380 |
| 2006/0149599 | A1* | 7/2006 | Fox et al. | 705/3 |
| 2007/0290028 | A1* | 12/2007 | Fox et al. | 235/375 |
| 2007/0290030 | A1* | 12/2007 | Fox et al. | 235/375 |
| 2008/0065424 | A1* | 3/2008 | Frick | 705/3 |

* cited by examiner

*Primary Examiner* — Tatyana Zalukaeva
*Assistant Examiner* — Benedict L Hanrahan
(74) *Attorney, Agent, or Firm* — Bernhard P Molldrem, Jr.

(57) ABSTRACT

A hand-held scanner appliance is employed to capture and display status of various types of catheter devices that have been inserted in hospital patients. The nurse scans his or her staff ID coded device, then scans the patient's ID wrist bracelets, and scans a catheter-unique identification coded tag on the catheter device. When the nurse performs a catheter insertion, and the catheter is scanned, a data entry is recorded with the patient identity, presence of catheter, and time of insertion. An intelligent rules engine computes the target removal time for the catheter device, which is also displayed. An alert for each catheterization occurs prior to the target removal time. The appliance is synchronized to the hospital server, and the catheterization status of the hospital patients is displayed for the medical practitioner. This process aids in preventing hospital-acquired infections.

6 Claims, 4 Drawing Sheets

○ AiCT-Mozilla Firefox   _ ▢ ✕

Indwelling Device Monitor

 Add Device

| Patient | Room | Device Type | Nurse | Insert Time | Expire Time | Elapsed Time |
|---|---|---|---|---|---|---|
| Buzz Brighton | 101 | Foley Catheter | Ginger Bayliss | 04/30/09 08:27:13 | 05/01/2009 08:27:13 | 26:04:42 |
| Hamilton Hammond | 102 | Supra-Pubic Catheter | Mary Jo Walsh | 04/30/09 09:15:13 | 05/01/2009 09:15:13 | 25:16:42 |
| Sam Flagg | 103 | Arterial Line | Margaret Houlihan | 04/30/09 09:28:25 | 05/01/2009 09:28:25 | 25:03:30 |
| Calvin Spalding | 104 | Intravenous Catheter | Kealani Kellye | 04/30/09 10:27:49 | 05/01/2009 10:27:49 | 24:04:06 |
| Crandell Clayton | 105 | Arterial Line | Ginger Bayliss | 04/30/09 10:29:01 | 05/01/2009 10:29:01 | 24:02:54 |
| M.P. Muldoon | 106 | Supra-Pubic Catheter | Mary Jo Walsh | 04/30/09 11:21:13 | 05/01/2009 11:21:13 | 23:10:42 |
| Sam Pak | 107 | Foley Catheter | Margaret Houlihan | 04/30/09 11:26:01 | 05/01/2009 11:26:01 | 23:05:54 |
| Bartford Steele | 108 | Intravenous Catheter | Kealani Kellye | 04/30/09 11:27:17 | 05/01/2009 11:27:17 | 23:04:38 |
| Igor Straminsky | 109 | Foley Catheter | Ginger Bayliss | 04/30/09 11:27:49 | 05/01/2009 11:27:49 | 23:04:06 |
| Jonathan S. Tuttle | 110 | Foley Catheter | Mary Jo Walsh | 04/30/09 11:28:07 | 05/01/2009 11:28:07 | 23:03:48 |
| Donald Penobscot | 111 | Arterial Line | Margaret Houlihan | 04/30/09 19:03:13 | 05/01/2009 19:03:13 | 15:28:42 |
| Zelmo Zole | 112 | Supra-Pubic Catheter | Ginger Bayliss | 04/30/09 21:33:13 | 05/01/2009 21:33:13 | 12:58:42 |
| Jack Scully | 113 | Supra-Pubic Catheter | Mary Jo Walsh | 05/01/09 01:11:01 | 05/02/2009 01:11:01 | 09:20:54 |
| Luther Rizzo | 114 | Arterial Line | | 05/01/09 02:51:13 | 05/02/2009 02:51:13 | 07:40:42 |
| Sidney Freedman | 115 | Foley Catheter | Kealani Kellye | 05/01/09 04:38:01 | 05/02/2009 04:38:01 | 05:53:54 |
| Walter Peterson | 117 | Foley Catheter | Margaret Houlihan | 05/01/09 10:33:07 | 05/02/2009 10:33:07 | 00:00:06 |

Last Updated: 10:31:55

Done

FIG.5

CUI-TAGGED CATHETER DEVICES AND SYSTEM

CONTINUING APPLICATION DATA

This is a Continuation-in-Part of our copending application Ser. No. 12/116,579, filed May 7, 2008

BACKGROUND OF THE INVENTION

This invention relates to a technique of accounting for the presence of medical equipment that is placed in intimate contact with a patient's tissues, such a urinary catheter or other indwelling catheter in a hospital patient, and is more specifically concerned with a technique that permits scanning of the patient with a scanning device for that purpose. The invention is more specifically concerned with a technique for indicating the presence or absence of a catheter, the term "catheter" to including an IV tube, a wound dressing, or other item that can create a source of a hospital-acquired infection if the device remains in contact with a hospital patient for an extended period. The invention is also concerned with techniques for maintaining a log of patients with catheters and of the time and date when the catheters are scheduled to be removed.

The invention is more particularly concerned with a technique that employs an identification tag, e.g., uniquely coded radio frequency identity (RFID) chips or tags and one or more RFID scanners adapted to track the use of the catheters. For some applications, an alternative identification tag may be used, such as a mag stripe, a two-dimensional bar code or a one-dimensional bar code.

Hospital-acquired infections of patients, at the current time, are a major problem in medicine, both as a significant drawback to patient care, and also as a significant cost to hospitals, a cost which is not reimbursable. Urinary tract infection, or UTI, is the most common hospital-acquired infection, and UTIs have been linked to the use of urinary catheters. Urinary catheters can serve as an example of an application of this invention, but other catheters or catheter related devices present similar problems. At present, one in four hospitalized patients is fitted with a urinary catheter. Each year, urinary catheters trigger a half million or more cases of urinary tract infection. However, many patients do not require catheters, and many others do not need them beyond a day or two of their hospitalization. Urinary catheters are often ordered only as a precaution after some types of surgeries. Hospitals do not have any reliable system to track catheter use, and many hospitals do not keep track of which patients have catheters. It is estimated that only about one in ten hospitals conducts a daily check of the patient to see if continued catheter use is needed. As a result,] a large share of hospital patients have catheters for several days longer than is necessary, and this extended use of urinary catheters leads to UTIs. About one percent of the patients administered a urinary catheter will get a urinary tract infection. All of those patients will require antibiotics, and some of them at least will suffer life-threatening complications.

The added cost of treating a patient for a hospital-acquired urinary tract infection is significant. Each episode of symptomatic nosocomial UTI costs at least $600, and each episode of UTI-related bloodstream infection results in even higher costs, conservatively at least $2,800. The problem is compounded in that many infections are asymptomatic, and patients can be administered an antibiotic simply for the reason that they have an indwelling catheter. The administration of an antibiotic can be inappropriate, as it can enable the infectious organisms to become multi-drug resistant, and very difficult to treat later on.

Moreover, many third-party payers, e.g., health insurance plans, do not or will no longer reimburse hospitals for hospital-acquired preventable complications. Medicare has instituted a "Never Events" policy, and will no longer pay for various preventable hospital errors, including not only surgical errors and injuries from falls, but also catheter-related urinary tract infections. The hospital cannot bill the injured patients for the added costs of treatment. The only recourse is for the medical practicioners to ensure the catheter is not left in when it is not needed.

Catheters are widely used even though need for urinary catheters is often unjustified and is unnecessary for most patients for about one-third of the days that the patients are catheterized. Moreover, the treating physician can often be completely unaware that a catheter is in place. A majority of hospitals do not monitor for catheter duration. As a result, the physicians are not writing orders to have the catheters removed, even when they are unnecessary or no longer necessary. It has thus become incumbent on the patient, or the patient's family, to ask the doctor or nurse, every day, whether the catheter is still really necessary or if it can be removed, but the patient or his or her family does not know they should do this, and it should not be the patient's burden to have to remind the doctor or nurse about the catheter.

In the past, some steps have been taken to reduce the incidence of catheter-related UTI. These include the use of catheters that are coated with an anti-bacterial agent to inhibit bacterial growth, or the use of an anti-microbial agent in the urine collection bag. However, these have not proven to be effective in reducing UTI. Other techniques involve using condom-style catheters, which at least reduce the risk of bacteria entering the urethra, or supra-pubic catheters, but the latter involves actually having to penetrate the abdomen and bladder of the patient, and can result in complications. Portable ultrasound bladder scanners can be used to see if the patient's bladder is being emptied without a catheter, but most hospitals do not use that system on any regular basis.

Accordingly, some simple technique is needed to identify those patients that have an indwelling catheter such as urinary catheter, to track the time of use of the catheter, and to ensure that the catheter is not left in place any longer than necessary. By removing the catheter as soon as it is no longer needed, the major cause of hospital-caused UTI will be avoided, and the cost and medical risk involved in hospitalization will be reduced significantly. The problems of this nature are not limited to urinary catheters. This technique can also be used for any other indwelling catheter, or to the use of catheter related devices or catheter-like devices That is, the invention can be used in situations where the use of a device that is in intimate contact with patient tissues heeds to be monitored, and the length of use of the device needs to be limited or controlled. This extends then to intravenous devices, including needles and tubes and also IV administrative sets and their associated tubing, in order to limit the possibility of septicemia or blood poisoning.

OBJECTS AND SUMMARY OF THE INVENTION

It is therefore an object of the present invention to improve the techniques used in tracking catheter use, in identifying which patients have a catheter, and in tracking the duration of catheter use for those patients.

A related object of this invention is to remove or avoid major causes of hospital-acquired urinary tract infections and other hospital acquired diseases.

A further object of the present invention is to provide a technique that is simple for the nurse or other practitioner to employ when catheterizing a patient and when later visiting the patient, and which provide the nurse or other practitioner the information necessary to decide when to remove the catheter from the patient.

Another object of the present invention is to provide a means of tracking catheter use which is compatible with the hospital computer network.

According to an aspect of this invention, there is a supply of catheters or catheter related devices, e.g., urinary catheters for the hospital patients for whom a catheter has been prescribed. Each catheter typically includes a flexible tube adapted to be inserted into intimate patient contact, i.e, in the case of a urinary catheter, within the urethra, i.e., urine duct, of the patient and to remain in place until removed. An external portion of the catheter has a fitting adapted to be attached to a drainage bag or other urine collection receptacle. Catheter tags, that is, catheter-unique identifiers (CUIs), e.g., RFID tags, each having a unique scannable ID code, are attached onto or incorporated onto the external part of the catheter for uniquely identifying each urinary or other catheter. The patients are provided with patient identity wrist bracelets, each incorporating a respective patient RFID tag. The bracelet RFID tags each have a unique scannable ID code uniquely identifying the associated patient. In some applications, a different system can be used for the CUI catheter tag and/or the bracelet, e.g., 1-D bar codes, 2-D bar codes, or magnetic stripes, or data bars such as GS1-DataBars.

The nurse is provided with a hand-held scanner device that is adapted for scanning the catheter CUI tags and the patient identification tags. The device has a display visible to the nurse, a suitably programmed internal processor, and software which begins an insertion sequence upon the scanning of the patient ID tag. After the patient bracelet ID tag is scanned in, the nurse scans the CUI tag of one of the catheters, and then re-scans the catheter tag. This produces a time stamp of a successful catheter insertion upon the second scanning of the catheter CUI tag. A log entry is created in the device indicating successful catheter insertion and time of insertion, as well as identity of the patient. This information is stored and displayed. The information is visible to the practitioner including the patient identity, presence or absence of one of the catheters in the said patient, and time of insertion of the catheter in the patient. The duration of the catheter is then tracked, either in terms of the length of time that the catheter has been in place, or in terms of the time remaining until the catheter is scheduled to be removed.

Where the urinary catheter is a Foley catheter, i.e., the type having an inflation port, the associated RFID tag can be affixed onto the inflation port.

An application server for this system is capable of communicating with the hand-held device(s) for storing patient data and catheter data based on information scanned into the hand-held device. The application server has embedded software for producing report(s) listing the identity of each patient who has been administered a catheter, and listing an associated targeted removal time for each such patient.

The hand held scanning device can display a listing of all the patients (for a given floor or for a given nursing station responsibility) as well as a listing of the targeted removal times. The device can also have an operator-actuated status switch to enter a removal of a catheter from the patient. The hand-held device favorably has a capability for displaying the individual patient identity and target time for removal of catheter upon scanning of the wrist bracelet of the that individual patient.

The hand-held device synchronizes with a central server by communicating with the server, either wirelessly or by means of a docking station. This provides current catheterization status to the central computer network, and that can be uploaded onto other similar hand-held scanner devices.

This technique makes it possible for nurses and treating physicians to recognize which patients have a catheter in place, and the duration of the catheterization, so that the doctor can make an informed decision to remove or retain the catheter for each patient. The catheter removal orders can be uploaded to the hand held devices, and displayed for each patient.

The catheter RFID or other CUI tag can also be scanned by the hand held device or by any other suitable scanner device for the purpose of alerting practicioners to the fact that there is a catheter in place.

For a better understanding of these and other objects and advantages of the present invention, reference will be made to the following detailed description of a preferred embodiment of the invention which is to be read in conjunction with the accompanying Drawing Figures.

BRIEF DESCRIPTION OF THE DRAWING

FIG. 5 is a screen showing a record of all catheter devices being monitored for a typical hospital ward, according to one example embodying this invention.

DETAILED DESCRIPTION OF A PREFERRED EMBODIMENT

Figures 1, 2:
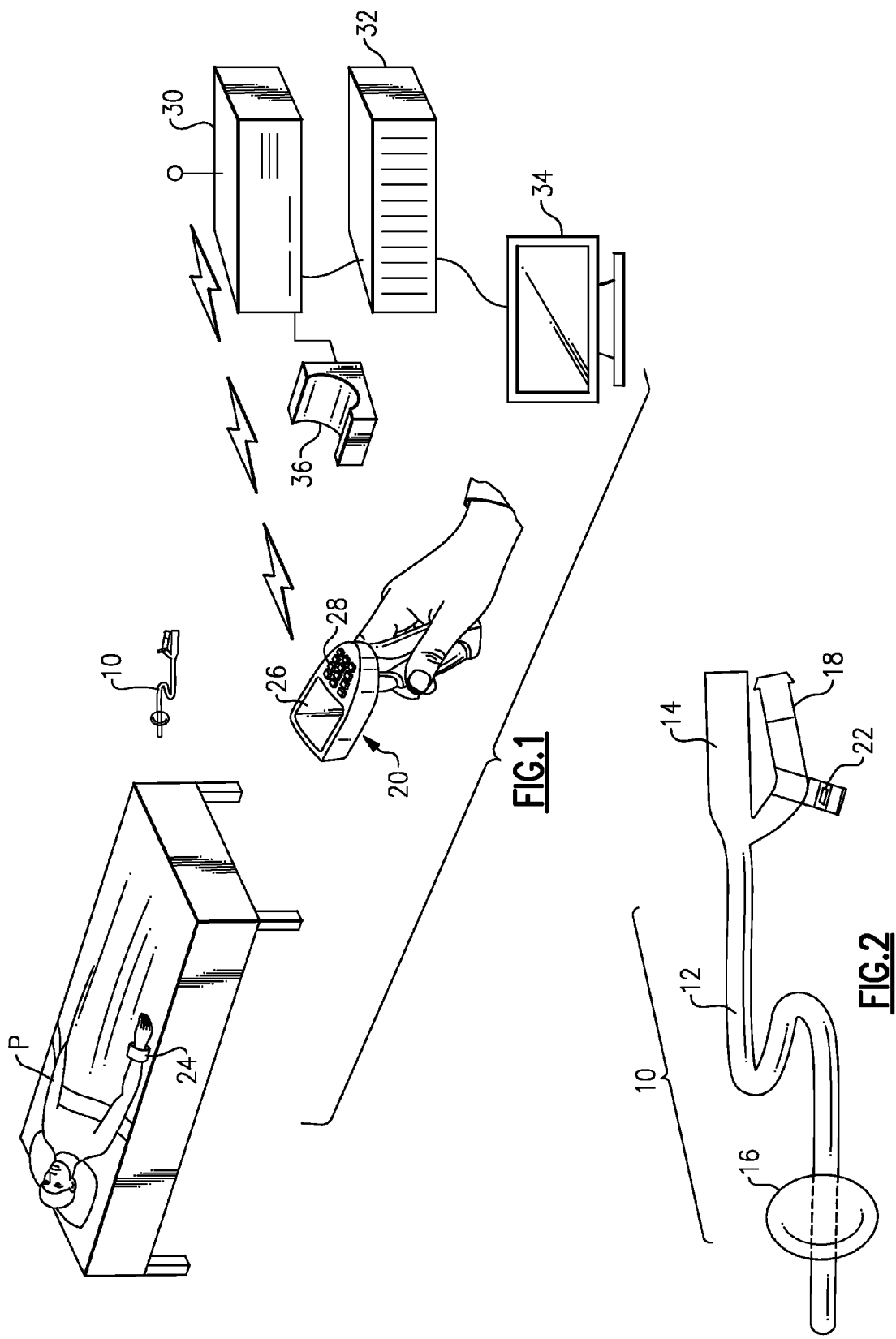
FIG. 1 is a general schematic view illustrating the equipment and usage of the RFID-based urinary catheter monitoring system according to one embodiment of the invention.
FIG. 2 shows a typical Foley type catheter, provided with an RFID tag, as employed in this embodiment.

Referring now to the Drawing, FIG. 1 illustrates the general arrangement of the equipment employed in this invention. A hospital patient P may be provided with a catheter 10, shown in more detail in FIG. 2, which is inserted into the patient P to assist in the drainage and collection of urine. The catheter remains in place for some period of time, and is considered an indwelling catheter. Also shown in FIG. 1 is a hand-held scanning appliance 20 capable of scanning and reading radio-frequency codes from RFID devices, as well as an application server 30. Here the RFID scanning appliance 20 and the server 30 are shown as communicating via a radio link, but the two devices may communicate via other means, such as a docking station 36 for the appliance 20.

As shown in FIG. 2 the catheter 10 is formed of an elongated flexible hollow tube 12 that is to be inserted via the patient's urethra into the bladder. There is drainage port 14 at the external terminus, and this is designed to connect to a urine drainage bag or other collection means (not shown). There is a balloon 16 positioned at the distal end of the tube 12 near the tip. After insertion, the balloon 16 is inflated with distilled water, which is injected through an inflation port 18 at the external end of the catheter 10. The inflated balloon 16 keeps the tube 12 from being ejected from the patient's bladder, but can be easily deflated for decatheterization by draining the water out the inflation port 18.

In this case, the catheter 10 has an catheter-unique identification tag, here an RFID tag 22, attached onto the external end, e.g., on the inflation port 18. This RFID tag 22 contains a unique code that can be transmitted to the scanner appliance 20 when the tag 22 is interrogated, and that code identifies the specific catheter 10. Each other catheter will have a similar tag 22, each with an individual unique code.

Returning to FIG. 1, The patient P is provided with patient identification bracelet or wrist-band 24, and each wrist-band has an embedded RFID tag containing a unique RFID code that uniquely identifies the patient.

As also shown in FIG. 1, the hand held scanner appliance 20 has a screen or display 26 for displaying patient and catheter information, and also has a keypad 28 for entering data or for commencing an operation, i.e., catheter insertion or removal. Instead of a keypad, the appliance could use a touch screen to serve the purposes of both display screen and keypad. The term "hand held scanner appliance" should be interpreted broadly enough to cover the wheeled-in portable computer devices that are often used by nurses and other care providers in a hospital environment.

The application server 30 is connected to a hospital computer network 32, and that network may be accessed at various stations, represented here by a computer monitor screen 34.

Each patient P is uniquely assigned an RFID bracelet 24. This bracelet is associated with data in the application server 30, to include patient identity and location (name, room assignment, etc.), name of treating physician, as well as other relevant treatment information for that patient. The application server 30 maintains data about all patients who currently host a catheter, as well as the time of catheterization. The application server also tracks catheterization orders and removal orders. Target removal time(s) are configurable at the application server.

The software application running on the server 30 will provide an interface for pending catheterization requests to be entered. The server software application displays a list of the catheterizations that are pending, and whether of not these are initial catheterizations, removals, or replacements. The application provides the nurse(s) with a list of catheterization procedures to be performed, and how many catheters and bracelets will be needed to complete them.

The nurse, or other practitioner who is to perform the catheterization procedure, first retrieves an RFID catheter 10, and a portable scanner appliance 20. If this is an initial catheterization for the patient P, the patient's RFID bracelet 24 is also obtained and placed on his/her wrist. The patient identity is entered into the system by the scan of the bracelet 24.

In the patient room, the bracelet 24 is scanned. The patient's name and other identifying data as indicated by the RFID scanner appliance on the display 26 are compared with the patient's chart. If this is the patient's first catheter, the bracelet is applied to the patient at this time, and scanned in, i.e., applied both physically and logically. The catheter 10 is scanned prior to insertion. The RFID scanner appliance 20 then associates the scanned catheter 10 with the patient P. The catheter is inserted in the patient. If the insertion is successful, the catheter 10 is re-scanned, and at that time the RFID scanner appliance 20 considers the procedure complete, and a timestamp is recorded. If there is some problem with this catheter, and it cannot be inserted, the nurse may scan a second catheter 10, which has its own RFID tag 22. This logically terminates the insertion of the first catheter and commences the insertion of the second one. Then, scanning the second catheter 10 after insertion indicates a successful insertion procedure, and creates the timestamp, as discussed before. Scanning the same catheter both prior to insertion and post-insertion indicates a successful procedure. Visual feedback, presented on the video display 26 of the scanner appliance 20, guides the nurse through this procedure.

The nurse can then perform the catheter procedures that have been ordered for a number of patients, using the same scanner appliance. Appliance 20 can transmit catheter transaction data back to the application server by the radio link, as illustrated. Alternatively, the appliance 20 can be returned to the docking station 36, which transfers data between the appliance and the server. Catheter transaction data are uploaded to the server at that time, and any updated data will be downloaded to the RFID scanner appliance 20, as appropriate.

Both the application that is running on the application server 30 and the embedded application software on the RFID scanner appliance 20 are capable of generating alert messages. These alert messages may be visual or audible, may involve email or text-messaging, or may leverage an external paging system. The alert messages remind the users, i.e., the medical practicioners, of specific patients for whom a catheter is due for replacement or removal, as well as those who are already overdue for replacement/removal.

The application server is capable of generating reports indicating which catheters are in need of replacement and/or removal within a given time span, i.e., during a nursing shift. These reports may be arranged in sequential time order, i.e. by target removal time, or may be listed in terms of room or floor sequence. The nurse may select the order that is best suited to use as a job checklist. The reports may be made available to the RFID scanner appliance 20, and may also be made available to computer monitor screen 34 at the nursing station. The data presented will be as current as the most recent synchronization of the RFID scanner appliance 20.

The display 26 of the appliance 20, while idle, shows a list of all the patients with catheter expiry times, as well as time remaining for each. When a given patient's wrist-band or bracelet 24 is scanned, then the appliance display 26 will show only the identity, expiration time, and time remaining for that patient P. Scanning a bracelet 24 followed by scanning of the RFID tag 22 of a catheter 10 will commence a catheter insertion workflow. The insertion workflow may be aborted by depressing one of the keys of the keypad 28. Scanning a catheter RFID tag 22 will present an interface with which the nurse can follow procedures on the screen 26 so as to indicate that the catheter has been successfully removed.

While an RFID tag or chip 22 is shown on a Foley urinary catheter in this embodiment, it should be understood that this technique can be employed for tracking the use of any sort of indwelling catheter. This system may be employed for veterinary as well as human medical purposes. There are other technologies that could be employed for embedding a unique identifying code on the catheter and on the patient bracelet. Rather than discrete tags 22, microscopic RFID chips, (RFID powder) may be incorporated into the material of the catheter device. In some cases, the bracelet may not be placed on the wrist, but may be more appropriately placed elsewhere on the patient.

As mentioned before, once the urinary catheter is inserted, the RFID tag or equivalent identification tag can be scanned by other devices to indicate to a treating physician or a nurse that there is a catheter present in the patient.

Because the system keeps accurate track of the insertion times and presence of these catheters in patients, and because the nurses and doctors are presented with an accurate and updated list of catheterizations, the physicians can make informed treatment decisions, so that the catheters can be removed as soon as they are no longer required. This will cut down significantly on the incidents of hospital-acquired UTI and other hospital-acquired infections, and will result in reduced costs and enhanced patient treatment success.

Other catheters and catheter-like medical devices likewise need to be monitored to reduce the risk of patient infection. These may include tracheotomy tubes, PEG feeding tubes, simple feeding tubes, endotracheal tubes, chest tubes, and abscess suction drainage tubes. In each case the tubes may be made with an integrated RFID tag or have one secured to them before being inserted in the patient. If the system is using a different CUI tag system, such as 2-dimensional bar-coded tags, then that type of tag may be pre-attached to the tube or attached before insertion. The monitoring system with CUI tags may also be used with intravenous systems, including the intravenous tubes and needles that actually penetrate the patient's skin, and also the IV administration sets that attach to the IV tubes.

Figure 3:
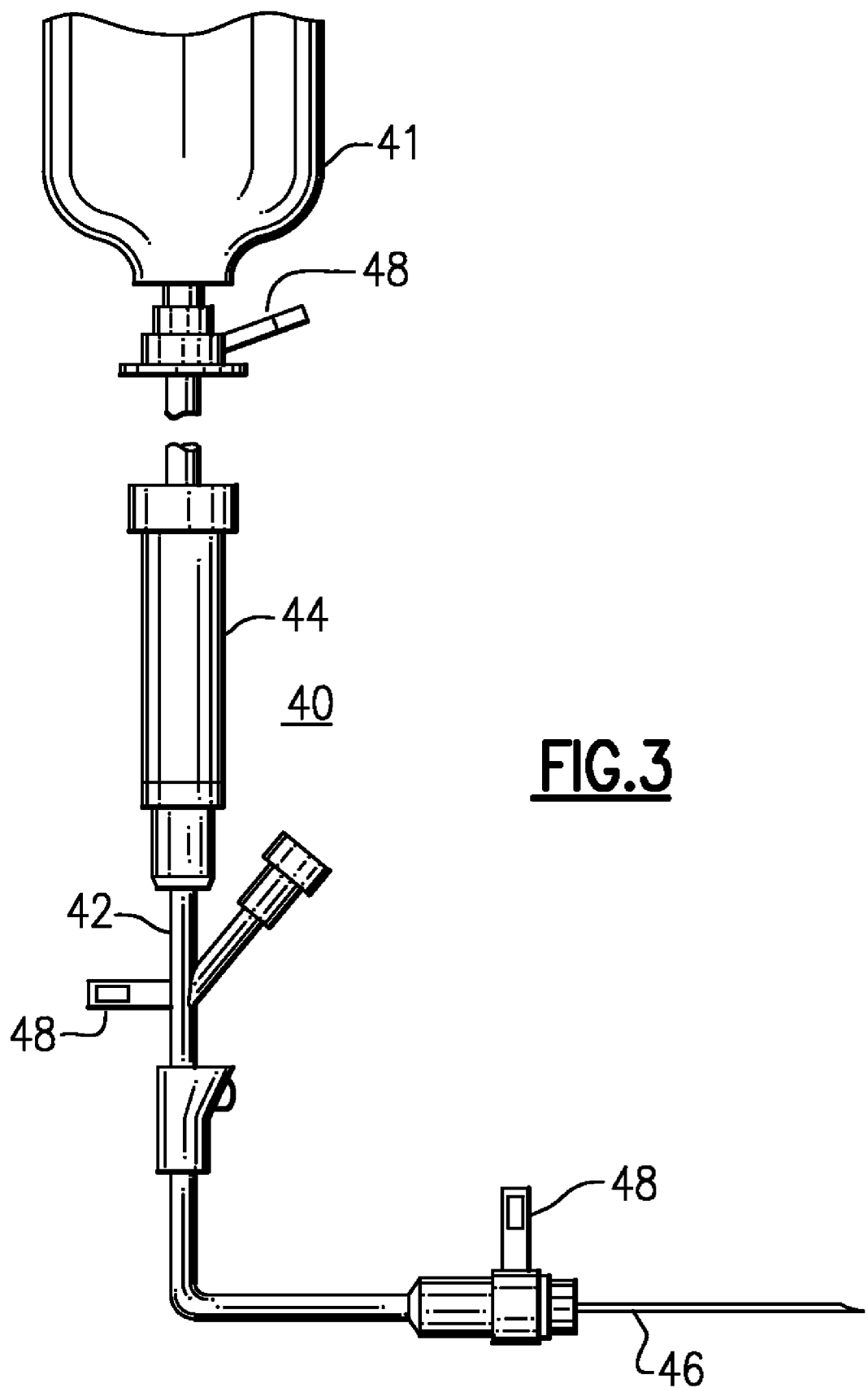
FIG. 3 shows an example of an intravenous line and associated intravenous administration set, incorporating the principles of this invention.

As shown in FIG. 3, a gravity flow IV arrangement or administration set 40 is provided for administering fluids intravenously to a patient. The administration set 40 can have one or several branches. Here, the set 40 has a bag 41 of blood, ringer's solution, or other sanitary fluid, a main IV line 42 with a drip chamber 44, and an IV tube leading to an intravenous needle 46 that is to be placed into a vein in the patient's arm or leg. In some cases, an auxiliary line can connect components of the administration set, e.g., above a junction of the main and shunt flow line. The latter may be used for a second or supplemental source of blood or an IV fluid. The set 40 can have one or more RFID tags 48, each with a distinct and unique identifier code to identify the type of IV administration set 40 or component, and to provide a unique code number for that administrative set. In this illustration, the IV administration set 40 has plural tags 48, each associated with a different component. This may be used for logging the times of insert or employment of the various components, so that system will provide the duty nurse with alerts for expiration of time of each component. For example, an IV administrative set and its associated tubing needs to be replaced in a patient at ninety-six hours of use, and the system can provide tracking and alerts on that basis.

As with the previous illustration of the urinary catheter, the tags 48 can be incorporated into the components of the administrative set 40, or stick-on tags may be attached adhesively to them at the time of insertion. In some cases, rather than employing RFID chips, the tags may incorporate a magnetic coded strip, or may have a bar coded optically read symbol. The dressing applied to the patient at the point of needle insertion can also be provided with an RFID tag 48, so that the system can compute a target replacement time for the dressing, and alert the nurse staff a pre-set amount of time before the target replacement time arrives.

These coded tags 48 may be used with other types of devices, as discussed earlier, such as tracheotomy tubes, feed tubes, abscess suction drainage tubes, or any other device that is to be kept in intimate contact with the patient's tissues, and for which prolonged use could possibly lead to an induced infection or other adverse consequence.

Figure 4:
FIG. 4 is a record creation screen as used by a nurse or other caregiver at the time that an indwelling catheter device is administered to a patient.

The system operation for monitoring and tracking an indwelling catheter (of any of a variety of catheter types) can be explained with reference to FIGS. 4 and 5. The indwelling catheter tracking system of this invention correlates each catheter with a particular staff member and a particular patient, then monitors catheter type and placement time, and applies replace/removal rules to determine alert times. Then the system reminds the nurse staff and reports catheter status for each catheterized patient. Each catheter or catheter-like device has a catheter unique identifier, i.e., a specific code carried on the associated RFID chip (or bar coded symbol), and this can be easily picked up by the associated scanner appliance 20. The appliance interfaces with the hospital server 30, and one or both is provided with software that includes an intelligent rules engine. The rules engine applies a predetermined rules protocol to compute the target removal time for each inserted catheter device. The intelligent rules engine can take into account the health of the specific patient and the type of catheter. The appliance software tracks time of placement or insert of each catheter and computes the expire time, and provides an alert to the nurse staff a predetermined time in advance of the expire time, i.e. at 22:00 hours for an expire time that is 24:00 hours from insert time. This depends on the patient and on the type of catheter. For example, if a patient is post-operative and has an indwelling urinary catheter inserted, then the system will notify at 22:00 hours to assess and remove the catheter prior to 24:00 hours. The system requires documentation of intent, and reasons, if a decision is made to continue the indwelling catheter beyond 24:00 hours. If the catheterization is continues, a reassessment reminder is produced for each twenty-four hour period.

If a patient is admitted with an indwelling catheter and no order is noted to continue the catheter beyond that day, then the system reminds the nurse staff, at 22:00 hours post-admission, to remove the catheter prior to 24:00 hours. Any decision to continue the indwelling catheter beyond that time requires documentation of intent and reasons. If a patient has an order for an indwelling catheter of a given type for some number of days N, the system will provide an alert to remind the nurse staff 2:00 hours prior to the end of the established catheterization order, to remove the catheter. Again, any decision to extend catheterization beyond the N days requires documentation of intent and reasons.

The system of logging in, monitoring and tracking of catheters is straightforward. Either an order is received for catheterization of a patient, or the patient is received with the catheter already inserted. Catheter supplies are obtained and taken to bedside. Patient identification is verified against the clinical information system (using the patient's coded bracelet). For a catheter order, the catheter is inserted according to organizational protocol. If the patient is received with an un-tagged catheter, then a stick-on identification tag is attached to the catheter and the catheter is logged in.

For each catheterization the associated catheter unique identifier (CUI) is captured and automatically entered into the system. Typically, the CUI is located at the distal end of the catheter, near a drainage tubing insertion site. The catheter CUI is associated with the specific patient by using the scanner appliance 20. If the catheter is without a CUI tag, one can be adhesively affixed to it. The staff member also associates herself or himself using a scanning process. Later if a new catheter is needed, the new CUI can be attached and re-associated. The data are uploaded to the hospital database wirelessly or from the docking station.

Status of the catheters for the patients in a given ward or throughout the hospital can appear on a status view on the scanner display 26 or on the monitor 34. Status rules are provided on a pop-up box that displays the associated rule. A status reminder or alert can be carried out as a defined status view presentation: a color-coded view of the patient and catheter record such that a catheter record within acceptable time parameters would be displayed in green; where a two-hour reminder sent the display would be in yellow; and for catheter records that are past their expire time i.e. beyond acceptable parameters, the display of the catheter records would be in red.

For statistical use, a summary of the records of catheter use by type can be generated, and if need be can be associated with any adverse events, such as infections.

A home version of this system can be used for out-patient care, long-term care or home care of a patient that may need catheter.

The procedure for creating a record during catheterization can be explained with reference to FIG. 4, which shows a pop-up window 50 that appears on the screen 26 of the scanner appliance, or on an equivalent display of a nurse's portable computer. There are three steps involved, and for each step this pop-up window 50 guides the practitioner through the steps to enter the data. First, the nurse or other staff person scans his or her own ID badge, which generates entry of the nurse name in the NURSE location. Then the nurse scans the patient's ID bracelet, and this generates the information that appears in the PATIENT and ROOM locations as the patient's name and patient room number. These should be visually verified at this time. Then, the indwelling device tag is scanned, and the device identity appears in the DEVICE location, which in this example is a Foley Catheter. The nurse then simply clicks on the CREATE RECORD button, and the patient catheterization data appears on the Indwelling Device Monitor view 52 (shown in FIG. 5). The entry for this patient appears as the last entry in this view. The view provides for each catheterized patient, the patient name, room number, type of catheter device, name of administering nurse, time of device insert, and target expire time. At the far right, the elapsed time is listed for each catheterization.

A similar pop-up screen (not shown) guides the nurse or other care giver through the procedures for removal of the catheter and updating of the catheterization records.

As shown in this example the target expire time is assumed to be 24:00 hours from insertion time. For the catheterizations that are within two hours of the target expire time, i.e., elapsed time greater than 22:00 and less than 23:59, the cathode expired time is presented in yellow on the screen (see area 54, hatched for the color yellow). For catheterizations in which the elapsed time since is greater than the target expire or removal time, i.e., more than 24:00, the expire time is shown in red (see area 56, lined for the color red).

The catheterizations that are in the safe zone, i.e., less than 22:00 hours elapsed time, are displayed in green.

For some particularly sensitive patients, a shorter target expire time may be observed, and this feature can be built into the software. Also, different devices can have different expire times, depending on the rules generated in the system for the different devices. Moreover, the names of the patients and nurses shown in FIGS. 4 and 5 are fictitious, and appear there only to serve as an example.

While this invention has been explained with reference to the particular structure disclosed herein, it is not confined to the details as set forth and this application is intended to cover any modifications and changes as may come within the scope of the following claims.

We claim:

1. Method of tracking indwelling catheter use in hospital patients, in which a plurality of scannable coded patient bracelets are placed upon respective ones of said hospital patients, and a plurality of catheters each having a catheter-unique identification (CUI) tag, each said bracelet having a unique patient identification code, and each said catheter CUI tag having a unique catheter identification code, wherein a computerized hospital information system contains patient demographic information including identity of each patient and room location of each patient and a designated health care practitioner responsible for inserting the catheter into the patient or patients possesses a coded device containing a scannable identification code, the method comprising:
    scanning the patient bracelet for one of said patients on a portable scanner appliance;
    selecting one of said catheters for insertion in the patient;
    scanning the CUI tag of the selected one of the catheters with the scanner appliance to commence a catheterization sequence in which the scanner appliance electronically associates the selected one of the catheters with said patient;
    scanning the designated health care practitioner coded device at the time of scanning the patient bracelet and the CUI tag of the catheter device inserted into the patient;
    after the scanning the CUI tag thereof, the designated health care practitioner inserting said catheter device in the patient;
    the scanner appliance synchronizing to said hospital information system the catheterization data to include identity location of each such patient, identity of the designated health care practitioner inserting the catheter, and date/time stamp of the insertion of each said catheter in said patients;
    and the scanner appliance applying a rules protocol to generate a target removal time for said catheter device and to display said target removal time along with identity of the patient to the designated health care practitioner.

2. The method of claim 1, further comprising creating a display on said scanner appliance showing a list of patients having catheters and associated catheterization data for said patients, including the associated target removal times.

3. The method of claim 1, wherein said step of synchronizing includes placing said appliance into a docking station that communicates with said hospital server.

4. The method of claim 1, wherein said hospital information system produces a report listing the identity of each patient who has been administered a catheter and lists the associated target removal time for each patient.

5. The method of claim 4, wherein the scanner appliance displays the report listing the identity of said patients, including for each said patient, the identity of the patient, the type of catheter device inserted in said patient, insertion time of the catheter device inserted in said patient, and the target removal time for the associated catheter device.

6. The method of claim 5, wherein the scanner appliance provides an alert for each listed patient when the elapsed time after the insertion time of the associated catheter device exceeds a predetermined alert time.

* * * * *